(12) United States Patent
Zhang et al.

(10) Patent No.: US 11,980,400 B1
(45) Date of Patent: May 14, 2024

(54) REDUCTION AND FIXATION DEVICE FOR FRACTURE CORRECTION

(71) Applicant: THE FIRST MEDICAL CENTER OF PEOPLE'S LIBERATION ARMY GENERAL HOSPITAL, Beijing (CN)

(72) Inventors: Lihai Zhang, Beijing (CN); Ye Peng, Beijing (CN); Gongzi Zhang, Beijing (CN); Shuwei Zhang, Beijing (CN); Shicheng Luo, Beijing (CN); Haobin Chen, Beijing (CN)

(73) Assignee: THE FIRST MEDICAL CENTER OF PEOPLE'S LIBERATION ARMY GENERAL HOSPITAL, Beijing (CN)

( * ) Notice: Subject to any disclaimer, the term of this patent is extended or adjusted under 35 U.S.C. 154(b) by 0 days.

(21) Appl. No.: 18/537,823

(22) Filed: Dec. 13, 2023

(30) Foreign Application Priority Data

Mar. 29, 2023 (CN) .......................... 202310315714.0

(51) Int. Cl.
*A61B 17/72* (2006.01)
*A61B 17/00* (2006.01)
*A61B 17/64* (2006.01)

(52) U.S. Cl.
CPC .... *A61B 17/7291* (2013.01); *A61B 17/00234* (2013.01); *A61B 17/645* (2013.01); *A61B 2017/00336* (2013.01)

(58) Field of Classification Search
CPC .......................... A61B 17/7291; A61B 17/645
See application file for complete search history.

(56) References Cited

U.S. PATENT DOCUMENTS 8,551,106 B2 * 10/2013 Harrold .............. A61B 17/7225
606/62
8,740,902 B2 * 6/2014 Brodsky ................ A61B 17/72
606/62

(Continued)

FOREIGN PATENT DOCUMENTS

CH          624570 A5     8/1981
CN       104983459 A    10/2015

(Continued)

OTHER PUBLICATIONS

Notice of Allowance of counterpart Chinese Patent Application No. 202310315714.0 dated May 15, 2023.

(Continued)

*Primary Examiner* — Andrew Yang (57) ABSTRACT

The invention provides a reduction and fixation device for fracture correction, and relates to the technical field of orthopedic medical devices. The reduction and fixation device for fracture correction comprises: an aiming frame body including a fixation plate, a first rectangular frame, a support plate and a second rectangular frame, wherein two first sliding frames are slidingly arranged in the first rectangular frame, a first screw sleeve is arranged in the first sliding frame, upper and lower sides of the first screw sleeve are rotationally connected to an inner wall of the first sliding frame through a first rotating shaft, a second sliding frame is slidingly arranged in the second rectangular frame, a second screw sleeve is arranged in the second sliding frame, and front and rear sides of the second screw sleeve are rotationally connected to an inner wall of the second sliding frame through a second rotating shaft.

8 Claims, 6 Drawing Sheets

(56) References Cited

U.S. PATENT DOCUMENTS 10,136,920 B2 * 11/2018 Fisher ................ A61B 17/6433
11,446,061 B2 * 9/2022 Early ................ A61B 17/8061

FOREIGN PATENT DOCUMENTS

| CN | 109009378 A | 12/2018 |
|----|-------------|---------|
| CN | 209074829 U | 7/2019 |
| CN | 209951508 U | 1/2020 |
| CN | 112869843 A | 6/2021 |
| CN | 216060712 U | 3/2022 |
| WO | 2013060948 A1 | 5/2013 |

OTHER PUBLICATIONS

First Office Action of counterpart Chinese Patent Application No. 202310315714.0 dated Apr. 28, 2023.

* cited by examiner

REDUCTION AND FIXATION DEVICE FOR FRACTURE CORRECTION

CROSS REFERENCE TO RELATED APPLICATIONS

The present application claims the benefit of Chinese Patent Application No. 202310315714.0 filed on Mar. 29, 2023, the contents of which are incorporated herein by reference in their entirety.

TECHNICAL FIELD

The invention relates to the technical field of orthopedic medical devices, and in particular to a reduction and fixation device for fracture correction.

BACKGROUND

The calcaneal fracture is a common fracture in trauma orthopedics. A patient with calcaneal fracture is often accompanied by high-energy violent injuries and soft tissue injuries, usually falling from a height. The surface skin is thin with a single blood supply, and incision complications such as cutaneous marginal necrosis often occur. The calcaneal fracture is always a difficult problem in clinical treatment. The improper treatment of calcaneal fracture can lead to persistent deformity and pain in the heel, and in severe cases, sequelae such as difficulty in walking may occur, which can seriously affect the postoperative function of the patient. In clinical practice, fewer soft tissues are covered around the calcaneus, and the fracture often affects the surrounding soft tissues, resulting in complications around the incision after the fracture, and even severe consequences such as infection and amputation, which greatly affect the quality of life of the patient. In the current clinical treatment, in order to treat fractures, doctors can only perform large incisions when the soft tissues are swollen, painful, and bruised and ecchymotic, because the fracture reduction is more difficult after the recovery of soft tissues is delayed for too long time. However, the traditional extended lateral approach for open reduction and internal fixation requires an arc-shaped postoperative incision of more than 10 cm, and the entire flap is turned up for surgery. The blood supply is greatly damaged, and the incidence rate of incision complications may be as high as 19% to 37%, including the following complications: the incidence rate of necrosis at the skin edge of incision is 2% to 10%, the rate of superficial infection of skin incision is 10% to 27%, and the rate of deep infection of skin incision is 1.3% to 2.5%. If the patient suffers from blood supply problems such as diabetic foot, smoking, lower extremity vascular disease, the incision complications of the calcaneal fracture will be more serious. After the extended lateral approach incision, the postoperative recovery of the patient is slow, and it is impossible to go down to the ground for rehabilitation training early, which has become a clinical problem that needs to be solved urgently.

In order to solve the above problem, the application with granted publication number "CN209074829U" discloses a reduction and fixation device for calcaneal fracture, including an aiming frame and a main nail. The aiming frame and the calcaneus are relatively positioned and fixed. The main nail is placed and positioned through a main aiming part so that the relative position and angle of the main nail and the calcaneus can be accurately positioned, and then the main nail is screwed into the patient's calcaneus; a first screw is placed and positioned through a first secondary aiming part, and then the first screw is screwed into the calcaneus and also screwed through a first threaded hole; a second screw is placed and positioned through a second secondary aiming part, and then the second screw is screwed into the calcaneus and also screwed through a second threaded hole. That is, the relative positions and angles of the first and second screws and the calcaneus are accurately positioned, and the relative positions and angles of the first and second screws and the main nail are accurately positioned. The main nail, the first screw and the second screw are cross-fitted, to reduce and fix the calcaneus fracture sites together, restore the length, width and height of the calcaneus, reduce and fix the posterior talar articular surface, reduce postoperative complications and reduce the risk of skin flap necrosis. However, the first secondary aiming part and the second secondary aiming part of this reduction and fixation device cannot be adjusted in angle, it is necessary to replace a new aiming frame to install the first screw and the second screw if the angles of the first threaded hole and the second threaded hole of the main nail change, and a variety of aiming frames are required for different installation angles, increasing the cost.

SUMMARY

The invention discloses a reduction and fixation device for fracture correction, including: an aiming frame body including a fixation plate, a first rectangular frame, a support plate and a second rectangular frame, wherein a main guide tube is arranged in the fixation plate, a main nail is arranged in the main guide tube, a front end of the fixation plate is fixedly connected to one end of the first rectangular frame, two first sliding frames are slidingly arranged in the first rectangular frame, a first screw sleeve is arranged in the first sliding frame, upper and lower sides of the first screw sleeve are rotationally connected to an inner wall of the first sliding frame through a first rotating shaft, a first guide tube is arranged in the first screw sleeve, a first screw is arranged in the first guide tube, the support plate is vertically arranged on an upper end of the fixation plate, the second rectangular frame is fixedly arranged on an upper end of the support plate, a second sliding frame is slidingly arranged in the second rectangular frame, a second screw sleeve is arranged in the second sliding frame, front and rear sides of the second screw sleeve are rotationally connected to an inner wall of the second sliding frame through a second rotating shaft, a second guide tube is arranged in the second screw sleeve, and a second screw is arranged in the second guide tube.

In some embodiments, the first rotating shaft is symmetrically arranged on the upper and lower sides of the first screw sleeve, and one end of the first rotating shaft is fixedly connected to an outer wall of the first screw sleeve, and other end of the first rotating shaft is rotationally connected to the inner wall of the first sliding frame; the second rotating shaft is symmetrically arranged on the front and rear sides of the second screw sleeve, one end of the second rotating shaft is fixedly connected to an outer wall of the second screw sleeve, and other end of the second rotating shaft is rotationally connected to the inner wall of the second sliding frame.

In some embodiments, two first threaded holes and one second threaded hole are arranged through the main nail, the first threaded hole is adapted to the first screw, and the second threaded hole is adapted to the second screw.

In some embodiments, an inner wall of the first screw sleeve is provided with a first internal thread, an outer wall of the first guide tube is provided with a first external thread, the first guide tube is connected to the first screw sleeve by threaded transmission, an inner wall of the second screw sleeve is provided with a second internal thread, an outer wall of the second guide tube is provided with a second external thread, and the second guide tube is connected to the second screw sleeve by threaded transmission.

In some embodiments, the two first sliding frames slide left and right along an inner wall of the first rectangular frame, a first screw rod is rotationally arranged on ends of the two first sliding frames away from each other, one end of the first screw rod away from the first sliding frame passes through an outer wall of the first rectangular frame, extends to outside of the first rectangular frame and is provided with a first knob, the first screw rod is connected to a penetration position of the first rectangular frame by threaded transmission; a second screw rod is rotationally arranged on a right side of the second sliding frame, one end of the second screw rod away from the second sliding frame passes through the second rectangular frame, extends to outside of the second rectangular frame and is provided with a second knob, and the second screw rod is connected to a penetration position of the second rectangular frame by threaded transmission.

In some embodiments, a rear end of the first guide tube is sheathed with a rotating ring, the rotating ring is connected to the outer wall of the first guide tube by threaded transmission, a rear end of the rotating ring is fixedly provided with a fixation tube, the fixation tube is sheathed outside the first guide tube, an inner diameter of the fixation tube is larger than an outer diameter of the first guide tube, a rear side wall of the fixation tube is provided with several first balls, the several first balls are distributed in a circular array with respect to a center of a rear side of the fixation tube, several pressing components are arranged behind the fixation tube, the several pressing components are distributed in a circular array with respect to a center of the first guide tube, the pressing components include a hinged plate, a pressing plate and a first spring, one end of the hinged plate is hingedly connected to the outer wall of the first guide tube, the pressing plate is located behind the hinged plate, the first spring is located between the pressing plate and the hinged plate, several first springs are provided, one end of the first spring is fixedly connected to a front side wall of the pressing plate, and other end of the first spring is fixedly connected to a rear side wall of the hinged plate.

In some embodiments, a horizontal plate is fixedly arranged on a rear end of the fixation plate and is perpendicular to the fixation plate, a third threaded hole and a guide hole are arranged in the horizontal plate, a third screw rod is arranged in the third threaded hole and is connected to the third threaded hole by threaded transmission, a front end of the third screw rod extends to the front of the horizontal plate and is rotationally provided with a clamping plate, a rear end of the third screw rod extends to the rear of the horizontal plate and is provided with a third knob, a guide rod is slidably arranged in the guide hole, one end of the guide rod is fixedly connected to a rear side wall of the clamping plate, a number of protection components are arranged at equal intervals in front of the clamping plate, the protection components include a cannula, a rear end of the cannula is fixedly connected to a front side wall of the horizontal plate, a sliding column is slidably arranged in the cannula, a guard plate is arrange on one end of the sliding column away from the cannula, a protective layer is fixedly arranged on a front side wall of the guard plate and is made of soft material, a second spring is arranged in the cannula, one end of the second spring is fixedly connected to a rear end of the sliding column, and other end of the second spring is fixedly connected to an inner wall of the cannula.

In some embodiments, a limit assembly is arranged behind the horizontal plate and includes a ratchet, the ratchet is fixedly arranged on the third screw rod, a fixation ring is arranged outside the ratchet, and an inner diameter of the fixation ring is larger than an outer diameter of the ratchet; a connecting rod is arranged between the fixation ring and the guide rod, one end of the connecting rod is fixedly connected to the guide rod, and other end of the connecting rod is fixedly connected to an outer wall of the fixation ring; the fixation ring is provided with a through hole, a limit rod is slidably arranged in the through hole, one end of the limit rod extends to inside of the fixation ring and abuts against an outer wall of the ratchet, one end of the limit rod close to the ratchet is adapted to gear teeth of the ratchet, one end of the limit rod away from the ratchet extends to outside of the fixation ring and is provided with a limit plate, a third spring is sheathed on the limit rod, one end of the third spring is fixedly connected to the limit plate, and other end of the third spring is fixedly connected to the outer wall of the fixation ring.

In some embodiments, the device further includes a fixation assembly configured to limit rotation of the first rotating shaft, wherein the fixation assembly includes two mounting plates arranged on one side of the first rotating shaft away from the first screw rod, the two mounting plates are vertically symmetrical about a center of the first screw sleeve, the mounting plate is fixedly connected to the inner wall of the first sliding frame, a third rotating shaft is rotationally arranged on a front end of the mounting plate, a gear is fixedly arranged on a front end of the third rotating shaft, a first gear rack is arranged on one side of the gear close to the inner wall of the first sliding frame and meshes with the gear, a rear side wall of the first gear rack is slidingly connected to a front side wall of the mounting plate, one end of the first gear rack extends to one side of the first rotating shaft close to the first screw rod and is provided with a first splint, other end of the first gear rack is fixedly connected to one end of a fourth spring, other end of the fourth spring is fixedly connected to a fixed block fixedly arranged on the front side wall of the mounting plate, a second gear rack is arranged on one side of the gear away from the first gear rack and meshes with the gear, a rear side wall of the second gear rack is slidingly connected to the front side wall of the mounting plate, the second gear rack is close to one side of the first rotating shaft and is provided with a second splint, other end of the second gear rack is provided with a second ball, a contact plate is arranged on one side of the second ball away from the first rotating shaft, upper and lower ends of the contact plate abut against upper and lower second balls respectively, a fourth screw rod is arranged on one end of the contact plate away from the first rotating shaft, one end of the fourth screw rod away from the first rotating shaft passes through the first sliding frame, extends to outside of the first sliding frame and is provided with a fourth knob, and the fourth screw rod is connected to a penetration position of the first sliding frame by threaded transmission.

In some embodiments, the first gear rack and the second gear rack are symmetrically distributed about a center of the third rotating shaft, a first arc-shaped groove is arranged on one side of the first splint close to the first rotating shaft, a first arc-shaped plate is arranged in the first arc-shaped groove, a second arc-shaped groove is arranged on one side of the second splint close to the first rotating shaft, a second arc-shaped plate is arranged in the second arc-shaped groove, and the first arc-shaped plate and the second arc-shaped plate are both made of rubber non-slip material.

BRIEF DESCRIPTION OF FIGURES

The accompanying drawings are used to provide the further understanding of the invention and constitute a part of the specification, and serve to explain the invention together with the embodiments of the invention but not limit the invention. In the accompanying drawings.

DETAILED DESCRIPTION

The preferred embodiments of the invention will be illustrated below in combination with the accompanying drawings, and it should be understood that the preferred embodiments illustrated here are only used to illustrate and explain the invention but not to limit the invention.

Furthermore, descriptions such as "first" and "second" in the invention are only for the purpose of description, but neither refer to the meaning of order or sequence nor limit the invention. They are only for the purpose of distinguishing the components or operations described by the same technical terms, but should not be understood as indicating or implying the relative importance or implicitly pointing out the number of indicated technical features. Therefore, the feature defined with "first" or "second" may explicitly or implicitly include at least one feature. In addition, the technical solutions and technical features of various embodiments may be combined with each other, but it must be on the basis of realizability by those ordinary skilled in the art. When the combination of technical solutions is contradictory or cannot be realized, it should be considered that such combination of technical solutions does not exist and is not within the scope of protection claimed by the invention.

Embodiment 1

The embodiment of the invention provides a reduction and fixation device for fracture correction, as shown in FIGS. 1-10, including: an aiming frame body including a fixation plate 1, a first rectangular frame 2, a support plate 3 and a second rectangular frame 4, where a main guide tube 5 is arranged in the fixation plate 1, a main nail 6 is arranged in the main guide tube 5, a front end of the fixation plate 1 is fixedly connected to one end of the first rectangular frame 2, two first sliding frames 7 are slidingly arranged in the first rectangular frame 2, a first screw sleeve 8 is arranged in the first sliding frame 7, upper and lower sides of the first screw sleeve 8 are rotationally connected to an inner wall of the first sliding frame 7 through a first rotating shaft 9, a first guide tube 10 is arranged in the first screw sleeve 8, a first screw 11 is arranged in the first guide tube 10, the support plate 3 is vertically arranged on an upper end of the fixation plate 1, the second rectangular frame 4 is fixedly arranged on an upper end of the support plate 3, a second sliding frame 12 is slidingly arranged in the second rectangular frame 4, a second screw sleeve 13 is arranged in the second sliding frame 12, front and rear sides of the second screw sleeve 13 are rotationally connected to an inner wall of the second sliding frame 12 through a second rotating shaft 14, a second guide tube 15 is arranged in the second screw sleeve 13, and a second screw 16 is arranged in the second guide tube 15.

The working principle and beneficial effect of the above-mentioned technical solution are as follows: when the aiming frame body is used, the main nail 6 is firstly placed in the main guide tube, the corresponding first screw 11 and second screw 16 are selected according to the first threaded hole and the second threaded hole on the main guide tube, and then the angles of the first guide tube 10 and the second guide tube 15 are respectively adjusted according to the angles of the first threaded hole and the second threaded hole; when the first guide tube 10 is adjusted, the first screw sleeve 8 can be manually rotated, the first screw sleeve 8 drives the first guide tube 10 to rotate, and the first guide tube 10 is aligned with the first threaded hole; and then the second screw sleeve 13 is manually rotated, the second screw sleeve 13 drives the second guide tube 15 to rotate, and the second guide tube 15 is aligned with the second threaded hole. At this time, the first screw 11 can be accurately installed in the first threaded hole through the guidance of the first guide tube 10, and the second screw 16 can be accurately installed in the second threaded hole through the guidance of the second guide tube 15. The main nail 6, the first screw 11 and the second screw 16 are cross-fitted to combine the fractured parts of the calcaneus together, thereby completing the reduction and fixation of the fractured parts of the calcaneus and ensuring the rapid healing of the fractured end. In the invention, since the first screw sleeve 8 is rotationally arranged in the first sliding frame 7 and the second screw sleeve 13 is rotationally arranged in the second sliding frame 12, the angles of the first guide tube 10 and the second guide tube 15 are respectively adjusted by rotating the first screw sleeve 8 and the second screw sleeve 13 according to the first threaded hole and the second threaded hole at different angles on the main nail 6, to thereby adjust the installation angles of the first screw 11 and the second screw 16, and increase the scope of application of the aiming frame body. One aiming frame body can complete the installation of various main nails 6, first screws 11 and second screws 16, reducing the medical cost and solve the technical problem of increasing the cost because the current reduction and fixation device requires a variety of aiming frames for installation angles of different first screws and second screws. The first sliding frame 7, the second sliding frame 12, the first rectangular frame 2 and the second rectangular frame 4 are all rectangular. The first sliding frame 7 can slide left and right in the first rectangular frame 2 to thereby adjust the position of the first sliding frame 7, and the position of the first screw sleeve 8 can be adjusted by adjusting the position of the first sliding frame 7; the second sliding frame 12 can slide left and right in the second rectangular frame 4 to thereby adjust the position of the second sliding frame 12, and the position of the second screw sleeve 13 can be adjusted by adjusting the position of the second sliding frame 12, achieving the effect of adjusting the installation positions of the first screw 11 and the second screw 16, making the scope of use of the aiming frame body wider, and further reducing the cost.

Embodiment 2

On the basis of the above-mentioned Embodiment 1, as shown in FIG. 1 to FIG. 9, the first rotating shaft 9 is symmetrically arranged on the upper and lower sides of the first screw sleeve 8, and one end of the first rotating shaft 9 is fixedly connected to an outer wall of the first screw sleeve 8, and other end of the first rotating shaft 9 is rotationally connected to the inner wall of the first sliding frame 7; the second rotating shaft 14 is symmetrically arranged on the front and rear sides of the second screw sleeve 13, one end of the second rotating shaft 14 is fixedly connected to an outer wall of the second screw sleeve 13, and other end of the second rotating shaft 14 is rotationally connected to the inner wall of the second sliding frame 12.

The working principle and beneficial effect of the above-mentioned technical solution are as follows: the first rotating shaft 9 is symmetrically arranged on the upper and lower sides of the first screw sleeve 8, the axial direction of the first rotating shaft 9 is perpendicular to the axial direction of the first screw sleeve 8, one end of the first rotating shaft 9 close to the first screw sleeve 8 is fixedly connected to the outer wall of the first screw sleeve 8, and one end of the first rotating shaft 9 away from the first screw sleeve 8 is rotationally connected to the inner wall of the first sliding frame 7, thereby realizing the rotational connection of the first screw sleeve 8, and facilitating the adjustment of the angle of the first guide tube 10. The front and rear sides of the second screw sleeve 13 are rotationally connected to the inner walls of the front and rear sides of the second sliding frame 12 through the second rotating shaft 14 respectively, so as to facilitate the adjustment of the angle of the second guide tube 15.

Embodiment 3

On the basis of Embodiment 1 or 2, two first threaded holes and one second threaded hole are arranged through the main nail 6, the first threaded hole is adapted to the first screw 11, and the second threaded hole is adapted to the second screw 16.

The working principle and beneficial effect of the above-mentioned technical solution are as follows: the first threaded hole is internally threaded with the first screw 11, and the second threaded hole is internally threaded with the second screw 16; and the fractured parts of the calcaneus can be reduced and fixed through the cross fit of the main nail 6, the first screw 11 and the second screw 16.

Embodiment 4

On the basis of any one of Embodiments 1-3, an inner wall of the first screw sleeve 8 is provided with a first internal thread, an outer wall of the first guide tube 10 is provided with a first external thread, the first guide tube 10 is connected to the first screw sleeve 8 by threaded transmission, an inner wall of the second screw sleeve 13 is provided with a second internal thread, an outer wall of the second guide tube 15 is provided with a second external thread, and the second guide tube 15 is connected to the second screw sleeve 13 by threaded transmission.

The working principle and beneficial effect of the above-mentioned technical solution are as follows: the first guide tube 10 is connected to the first screw sleeve 8 by threaded transmission; when the first guide tube 10 is installed, one end of the first guide tube 10 is aligned with the first internal thread of the first screw sleeve 8, and then the first guide tube 10 is rotated to fixedly install the first guide tube 10 in the first screw sleeve 8; and similarly, the second guide tube 15 can be installed in the second screw sleeve 13, so that the first guide tube 10 and the second guide tube 15 are installed more stably and reliably, and will not slide in the first screw sleeve 8 and the second screw sleeve 13 when used, which is convenient for use.

Embodiment 5

Figure 1:
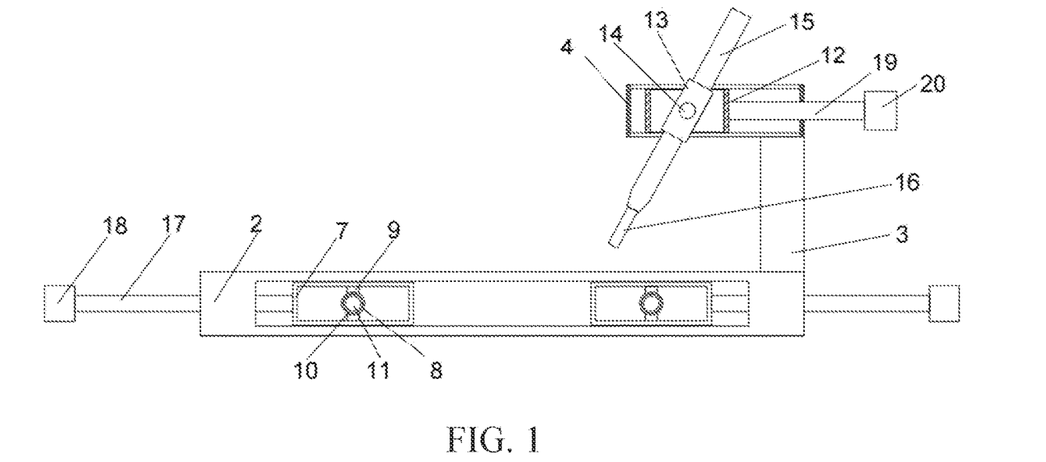
FIG. 1 is a schematic diagram of an overall structure of a reduction and fixation device for fracture correction in the invention.

On the basis of Embodiment 2, as shown in FIG. 1, the two first sliding frames 7 slide left and right along an inner wall of the first rectangular frame 2, a first screw rod 17 is rotationally arranged on ends of the two first sliding frames 7 away from each other, one end of the first screw rod 17 away from the first sliding frame 7 passes through an outer wall of the first rectangular frame 2, extends to outside of the first rectangular frame 2 and is provided with a first knob 18, the first screw rod 17 is connected to a penetration position of the first rectangular frame 2 by threaded transmission; a second screw rod 19 is rotationally arranged on a right side of the second sliding frame 12, one end of the second screw rod 19 away from the second sliding frame 12 passes through the second rectangular frame 4, extends to outside of the second rectangular frame 4 and is provided with a second knob 20, and the second screw rod 19 is connected to a penetration position of the second rectangular frame 4 by threaded transmission.

The working principle and beneficial effect of the above-mentioned technical solution are as follows: the first knob 18 is rotated, the first knob 18 drives the first screw rod 17 to rotate, and the rotation of the first screw rod 17 can drive the first sliding frame 7 to slide in the first rectangular frame 2. When the first sliding frame 7 is adjusted to the first target position which is the alignment position of the first screw 11 and the first threaded hole, the rotation of the first knob 18 is stopped, and the first sliding frame 7 will not slide in the first rectangular frame 2, improving the stability of the first sliding frame 7. Similarly, the rotation of the second knob 20 can drive the second sliding frame 12 to slide in the second rectangular frame 4 through the second screw rod 19, until the second sliding frame 12 is adjusted to the second target position, which is the alignment position of the second screw 16 and the second threaded hole. At this time, the first sliding frame 7 and the second sliding frame 12 remain fixed, which is helpful for the smooth installation of the first screw 11 and the second screw 16, and facilitates the start of fracture correction.

Embodiment 6

On the basis of Embodiment 4, as shown in FIG. 2 to FIG. 5, a rear end of the first guide tube 10 is sheathed with a rotating ring 21, the rotating ring 21 is connected to the outer wall of the first guide tube 10 by threaded transmission, a rear end of the rotating ring 21 is fixedly provided with a fixation tube 22, the fixation tube 22 is sheathed outside the first guide tube 10, an inner diameter of the fixation tube 22 is larger than an outer diameter of the first guide tube 10, a rear side wall of the fixation tube 22 is provided with several first balls 23, the several first balls 23 are distributed in a circular array with respect to a center of a rear side of the fixation tube 22, several pressing components are arranged behind the fixation tube 22, the several pressing components are distributed in a circular array with respect to a center of the first guide tube 10, the pressing components include a hinged plate 24, a pressing plate 25 and a first spring 26, one end of the hinged plate 24 is hingedly connected to the outer wall of the first guide tube 10, the pressing plate 25 is located behind the hinged plate 24, the first spring 26 is located between the pressing plate 25 and the hinged plate 24, several first springs 26 are provided, one end of the first spring 26 is fixedly connected to a front side wall of the pressing plate 25, and other end of the first spring 26 is fixedly connected to a rear side wall of the hinged plate 24.

The working principle and beneficial effect of the above-mentioned technical solution are as follows: before the first screw 11 is installed, the first guide rod 31 is firstly rotated to a preset position in which the first guide tube 10 is in contact with the outer skin of the patient's heel, then the rotating ring 21 is rotated, the rotating ring 21 rotates and moves axially along the first guide tube 10, the rotating ring 21 drives the fixation tube 22 to move close to the hinged plate 24, and the first ball 23 is in contact with the outer wall of the hinged plate 24, thereby driving the hinged plate 24 to move away from the first rectangular frame 2. The hinged plate 24 drives the pressing plate 25 to move away from the first rectangular frame 2 through the first spring 26, until the pressing plate 25 contacts the outer skin of the patient's heel. At this time, the pressing plate 25 can compress the fractured part of the calcaneus, improve the effect of reduction and fixation, prevent the misalignment of the fractured part when the first screw 11 is installed, and improve the rehabilitation effect of the patient.

Embodiment 7

Figure 2:
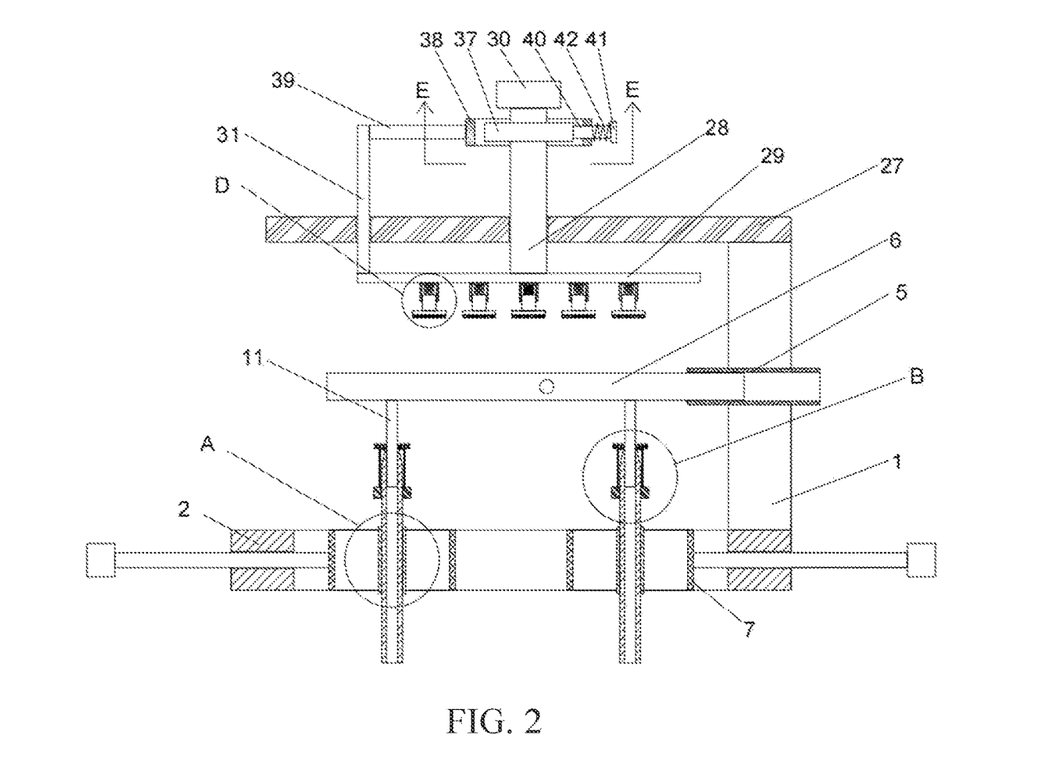
FIG. 2 is a top view of the reduction and fixation device for fracture correction in the invention.
Figure 3:
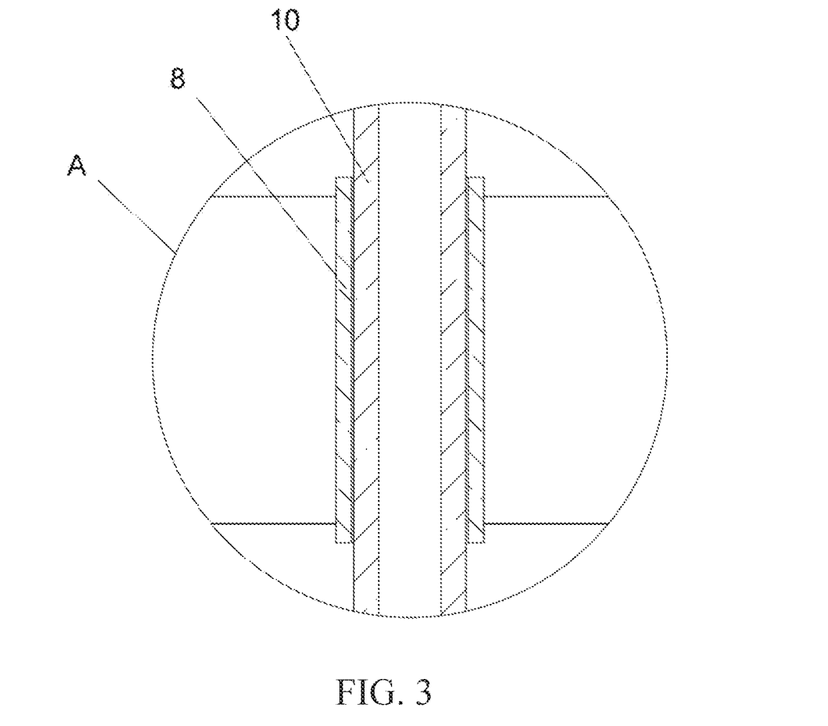
FIG. 3 is an enlarged view at A in FIG. 2 in the invention.
Figure 4:
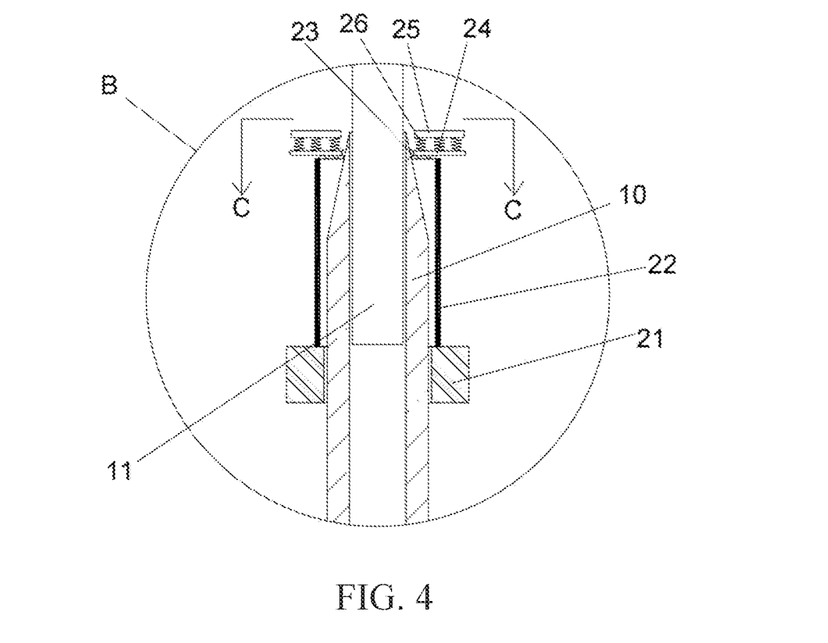
FIG. 4 is an enlarged view at B in FIG. 2 in the invention.
Figure 5:
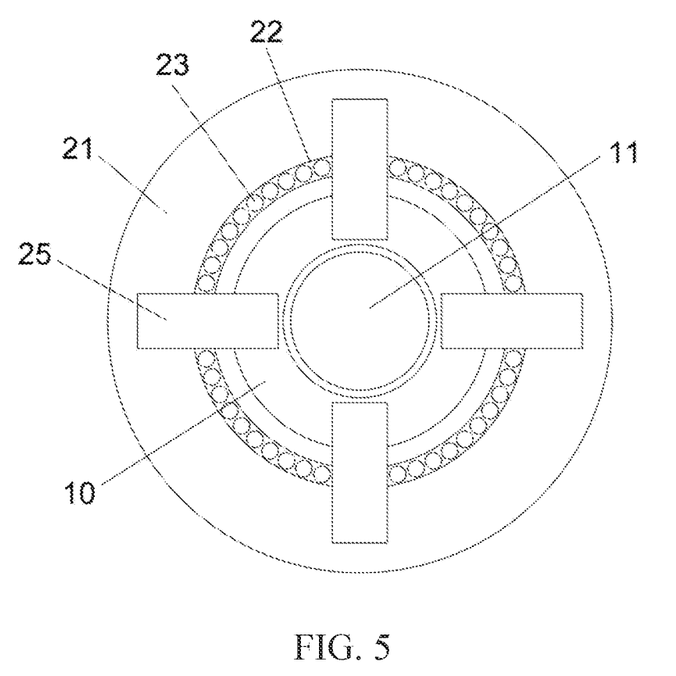
FIG. 5 is a partial section view at C-C in FIG. 4 in the invention.
Figure 6:
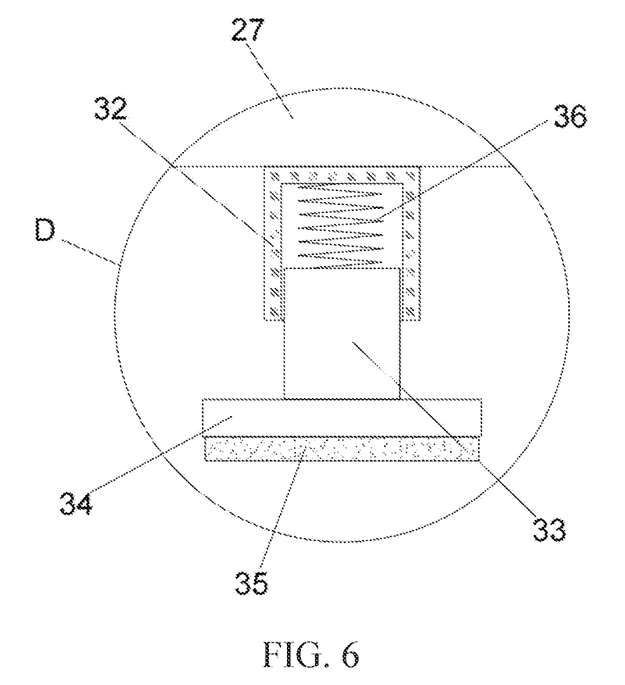
FIG. 6 is an enlarged view at D in FIG. 2 in the invention.
Figure 7:
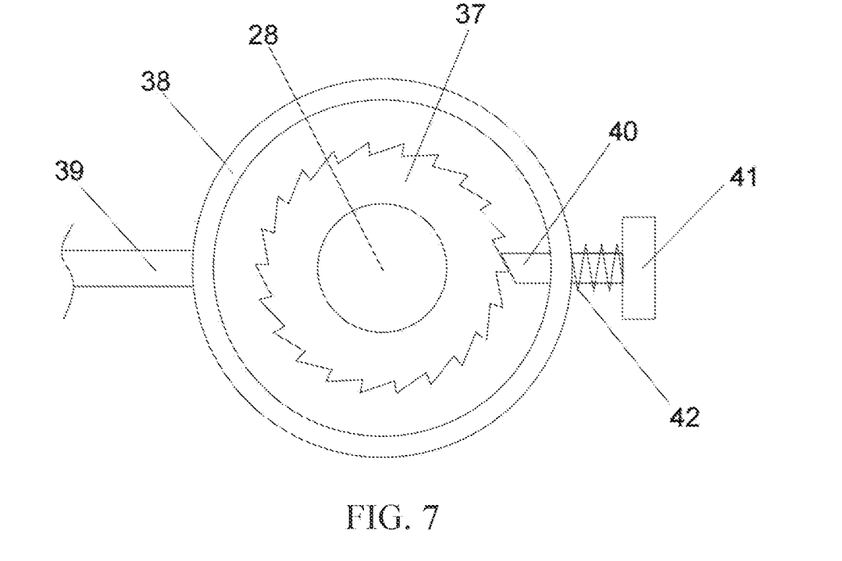
FIG. 7 is a partial section view at E-E in FIG. 2 in the invention.

On the basis of Embodiment 6, as shown in FIG. 2, FIG. 6 and FIG. 7, a horizontal plate 27 is fixedly arranged on a rear end of the fixation plate 1 and is perpendicular to the fixation plate 1, a third threaded hole and a guide hole are arranged in the horizontal plate 27, a third screw rod 28 is arranged in the third threaded hole and is connected to the third threaded hole by threaded transmission, a front end of the third screw rod 28 extends to the front of the horizontal plate 27 and is rotationally provided with a clamping plate 29, a rear end of the third screw rod 28 extends to the rear of the horizontal plate 27 and is provided with a third knob 30, a guide rod 31 is slidably arranged in the guide hole, one end of the guide rod 31 is fixedly connected to a rear side wall of the clamping plate 29, a number of protection components are arranged at equal intervals in front of the clamping plate 29, the protection components include a cannula 32, a rear end of the cannula 32 is fixedly connected to a front side wall of the horizontal plate 27, a sliding column 33 is slidably arranged in the cannula 32, a guard plate 34 is arrange on one end of the sliding column 33 away from the cannula 32, a protective layer 35 is fixedly arranged on a front side wall of the guard plate 34 and is made of soft material, a second spring 36 is arranged in the cannula 32, one end of the second spring 36 is fixedly connected to a rear end of the sliding column 33, and other end of the second spring 36 is fixedly connected to an inner wall of the cannula 32.

The working principle and beneficial effect of the above-mentioned technical solution are as follows: the third knob 30 is rotated, the rotation of the third knob 30 drives the rotation of the third screw rod 28, the third screw rod 28 moves in the third threaded hole towards the direction close to the first rectangular frame 2 through threaded transmission, the third screw rod 28 drives the clamping plate 29 to move towards the direction close to the first rectangular frame 2, and the clamping plate 29 drives the cannula 32 to move towards the direction close to the first rectangular frame 2. There are several cannulas 32 of which each is provided with a sliding column 33, the cannula 32 drives the guard plate 34 to move towards the direction close to the first rectangular frame 2 through the second spring 36 and the sliding column 33, until the protective layer 35 on the front side wall of the guard plate 34 contacts the outer skin of the patient's heel. Under the action of the second spring 36, the protective layer 35 is closely attached to the outer skin of the heel. The coaction of the protective layer 35 and the pressing plate 25 can compress the fractured parts of the heel together, further facilitating the reduction and fixation of the fractured parts of the calcaneus, and making the fixation more firm and stable. The protective layer 35 is made of soft material, and will not cause damage to the patient after contacting with the patient's skin, and is helpful for the recovery of the patient's fracture parts.

Embodiment 8

On the basis of Embodiment 7, as shown in FIG. 2, FIG. 6 and FIG. 7, a limit assembly is arranged behind the horizontal plate 27 and includes a ratchet 37, the ratchet 37 is fixedly arranged on the third screw rod 28, a fixation ring 38 is arranged outside the ratchet 37, and an inner diameter of the fixation ring 38 is larger than an outer diameter of the ratchet 37; a connecting rod 39 is arranged between the fixation ring 38 and the guide rod 31, one end of the connecting rod 39 is fixedly connected to the guide rod 31, and other end of the connecting rod 39 is fixedly connected to an outer wall of the fixation ring 38; the fixation ring 38 is provided with a through hole, a limit rod 40 is slidably arranged in the through hole, one end of the limit rod 40 extends to inside of the fixation ring 38 and abuts against an outer wall of the ratchet 37, one end of the limit rod 40 close to the ratchet 37 is adapted to gear teeth of the ratchet 37, one end of the limit rod 40 away from the ratchet 37 extends to outside of the fixation ring 38 and is provided with a limit plate 41, a third spring 42 is sheathed on the limit rod 40, one end of the third spring 42 is fixedly connected to the limit plate 41, and other end of the third spring 42 is fixedly connected to the outer wall of the fixation ring 38.

The working principle and beneficial effect of the above-mentioned technical solution are as follows: when the third screw rod 28 rotates towards the direction close to the first rectangular frame 2, the rotation of the third screw rod 28 drives the ratchet 37 to rotate; when the ratchet 37 rotates, the limit rod 40 slides along the outer wall of the ratchet 37. The guide rod 31 guides the movement of the clamping plate 29 until the protective layer 35 contacts the outer skin of the patient's heel. If the third knob 30 is rotated in the opposite direction, the limit rod 40 is stuck in the gear teeth of the ratchet 37, and the third screw rod 28 cannot rotate in the opposite direction. Only when the limit plate 41 is pulled away from the ratchet 37 to separate the limit rod 40 from the ratchet 37, can the third screw rod 28 be rotated in the opposite direction. The arrangement of the limit assembly can avoid the separation of the protective layer 35 from the outer skin of the patient's heel due to artificially touching the third knob 30 during the fracture correction process, thereby causing the fracture part to shift. The limit assembly can prevent the third screw rod 28 from rotating in the opposite direction, thereby improving the stability of the contact between the protective layer 35 and the outer skin of the patient's heel, helping the fracture correction of the patient, and improving the rehabilitation effect of the fracture.

Embodiment 9

Figure 8:
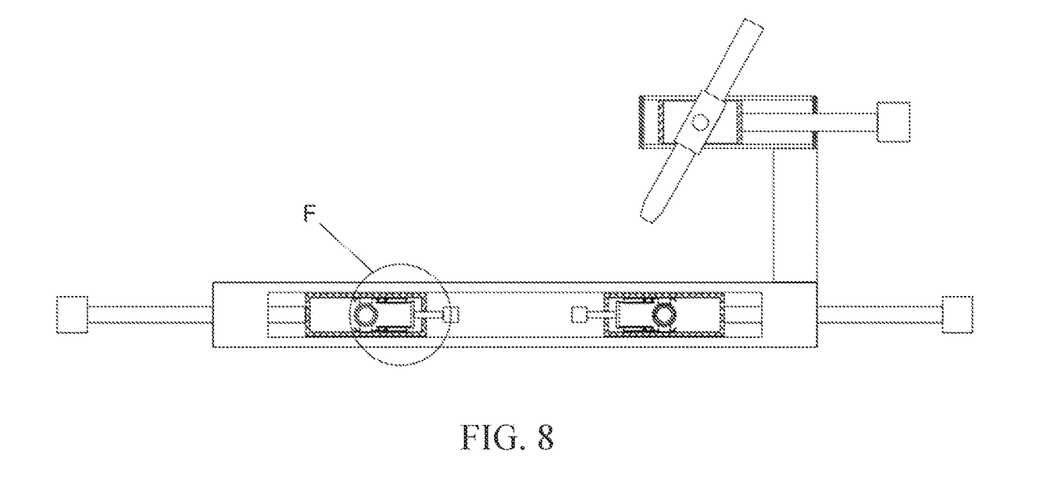
FIG. 8 is a schematic diagram of a fixation assembly in the invention.
Figure 9:
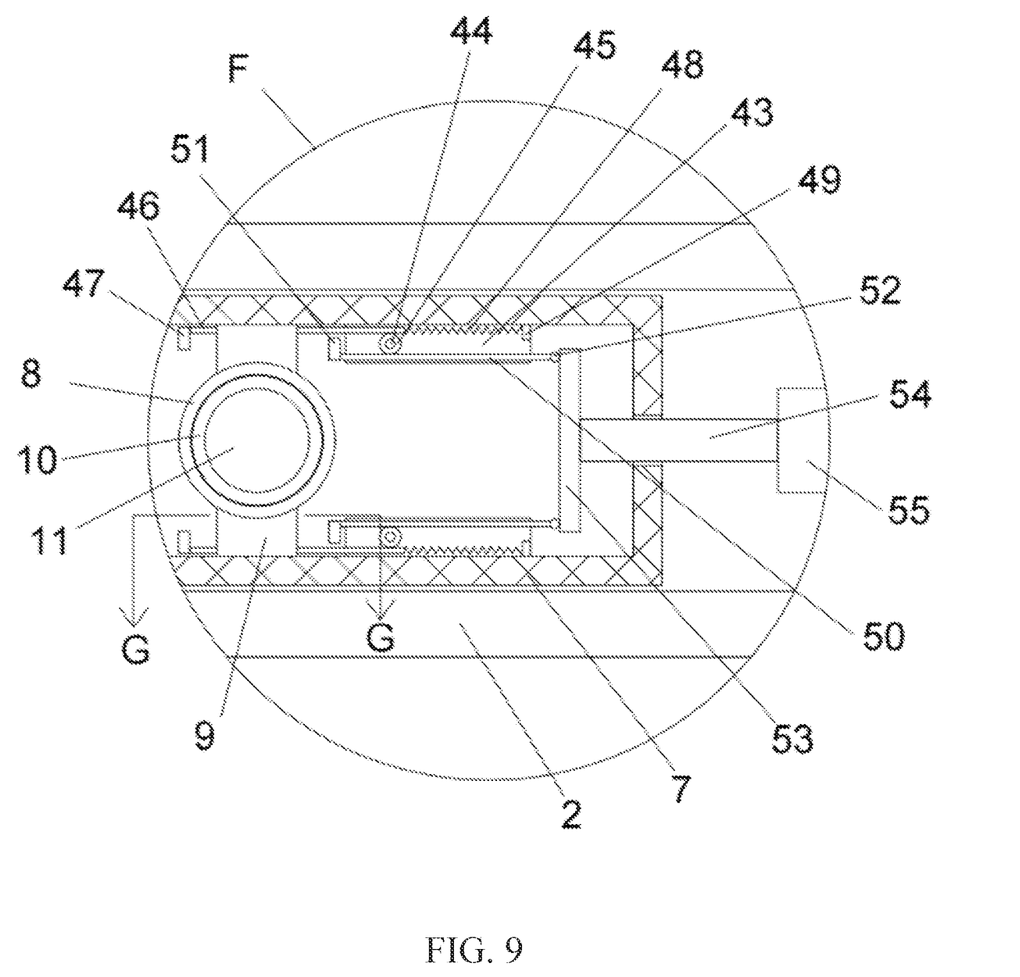
FIG. 9 is an enlarged view at F in FIG. 8 in the invention.
Figure 10:
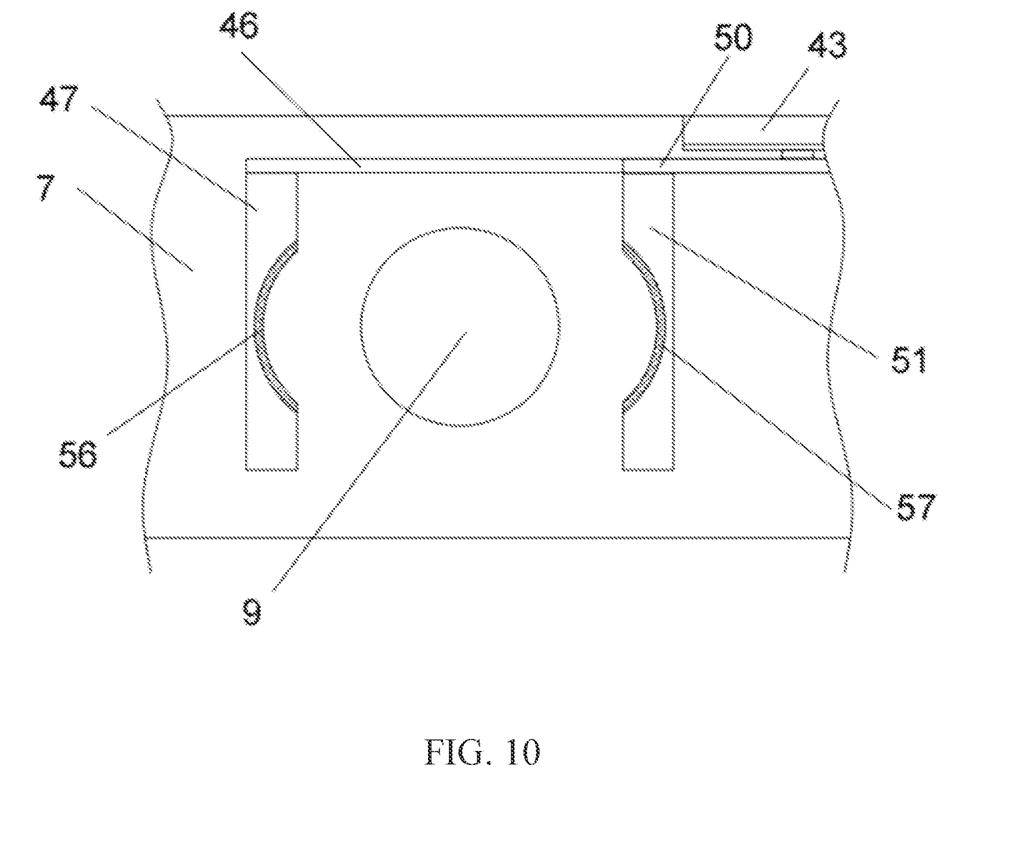
FIG. 10 is a partial section view at G-G in FIG. 9 in the invention.

On the basis of Embodiment 5, as shown in FIG. 8 to FIG. 10, the fixation assembly is configured to limit rotation of the first rotating shaft 9, the fixation assembly includes two mounting plates 43 arranged on one side of the first rotating shaft 9 away from the first screw rod 17, the two mounting plates 43 are vertically symmetrical about a center of the first screw sleeve 8, the mounting plate 43 is fixedly connected to the inner wall of the first sliding frame 7, a third rotating shaft 44 is rotationally arranged on a front end of the mounting plate 43, a gear 45 is fixedly arranged on a front end of the third rotating shaft 44, a first gear rack 46 is arranged on one side of the gear 45 close to the inner wall of the first sliding frame 7 and meshes with the gear 45, a rear side wall of the first gear rack 46 is slidingly connected to a front side wall of the mounting plate 43, one end of the first gear rack 46 extends to one side of the first rotating shaft 9 close to the first screw rod 17 and is provided with a first splint 47, other end of the first gear rack 46 is fixedly connected to one end of a fourth spring 48, other end of the fourth spring 48 is fixedly connected to a fixed block 49 fixedly arranged on the front side wall of the mounting plate 43, a second gear rack 50 is arranged on one side of the gear 45 away from the first gear rack 46 and meshes with the gear 45, a rear side wall of the second gear rack 50 is slidingly connected to the front side wall of the mounting plate 43, the second gear rack 50 is close to one side of the first rotating shaft 9 and is provided with a second splint 51, other end of the second gear rack 50 is provided with a second ball 52, a contact plate 53 is arranged on one side of the second ball 52 away from the first rotating shaft 9, upper and lower ends of the contact plate 53 abut against upper and lower second balls 52 respectively, a fourth screw rod 54 is arranged on one end of the contact plate 53 away from the first rotating shaft 9, one end of the fourth screw rod 54 away from the first rotating shaft 9 passes through the first sliding frame 7, extends to outside of the first sliding frame 7 and is provided with a fourth knob 55, and the fourth screw rod 54 is connected to a penetration position of the first sliding frame 7 by threaded transmission.

The working principle and beneficial effect of the above-mentioned technical solution are as follows: when the first screw 11 is aligned with the first threaded hole, the fourth knob 55 is rotated, the rotation of the fourth knob 55 drives the rotation of the fourth screw rod 54, the rotation of the fourth screw rod 54 drives the contact plate 53 to move towards the direction close to the first rotating shaft 9, the contact plate 53 abuts against the second ball 52 and drives the second gear rack 50 to move towards the direction close to the first rotating shaft 9, the second gear rack 50 slides horizontally on the front side wall of the mounting plate 43, and the second gear rack 50 drives the second splint 51 to move towards the direction close to the first rotating shaft 9. The movement of the second gear rack 50 drives the gear 45 to rotate at the same time, and the gear 45 drives the first gear rack 46 to move towards the direction close to the fixed block 49, where the first gear rack 46 is parallel to the second gear rack 50. The first gear rack 46 moves while the fourth spring 48 is compressed, the first splint 47 moves toward the direction close to the first rotating shaft 9, and the first splint 47 and the second splint 51 are in contact with the outer wall of the first rotating shaft 9 respectively. Under the common clamping effect of the first splint 47 and the second splint 51, the first rotating shaft 9 cannot rotate. The first rotating shaft 9 on the upper and lower sides can be fixed at the same time through the fixation assembly, and the first splint 47 and the second splint 51 fix the left and right sides of the first rotating shaft 9 respectively. Compared with unilateral fixation, the fixation effect is further improved, and the rotation of the first rotating shaft 9 is avoided. At this time, the first screw 11 can be installed. When the first screw 11 is installed, the first screw sleeve 8 will not rotate, and the first screw 11 will not be offset when installed, so that the first screw 11 is accurately installed in the first threaded hole, improving the accuracy of installation, and preventing the increased cost due to misalignment of the first screw 11 and the first threaded hole during installation; and the stability of the first guide tube 10 can be improved after installation, further ensuring the fracture correction effect and facilitating the rapid healing of the fractured parts. After the fracture correction is completed, the fourth knob 55 is rotated in the opposite direction to separate the first splint 47 and the second splint 51 from the first rotating shaft 9, facilitating the rotation and adjustment of the position of the first screw sleeve 8.

Embodiment 10

On the basis of Embodiment 9, as shown in FIG. 10, the first gear rack 46 and the second gear rack 50 are symmetrically distributed about a center of the third rotating shaft 44, a first arc-shaped groove is arranged on one side of the first splint 47 close to the first rotating shaft 9, a first arc-shaped plate 56 is arranged in the first arc-shaped groove, a second arc-shaped groove is arranged on one side of the second splint 51 close to the first rotating shaft 9, a second arc-shaped plate 57 is arranged in the second arc-shaped groove, and the first arc-shaped plate 56 and the second arc-shaped plate 57 are both made of rubber non-slip material.

The working principle and beneficial effect of the above-mentioned technical solution are as follows: the first arc-shaped groove is arranged on one side of the first splint 47 close to the first rotating shaft 9, the second arc-shaped groove is arranged on one side of the second splint 51 close to the second rotating shaft 14, and the first arc-shaped groove and the second arc-shaped groove are respectively adapted to the outer wall of the first rotating shaft 9. Finally, the first arc-shaped plate 56 in the first splint 47 and the second arc-shaped plate 57 in the second splint 51 are in contact with the first rotating shaft 9, thereby limiting the rotation of the first rotating shaft 9. The first arc-shaped plate 56 and the second arc-shaped plate 57 are made of rubber non-slip material, improving the non-slip performance of the first arc-shaped plate 56 and the second arc-shaped plate 57, and further fixing the first rotating shaft 9.

Evidently those skilled in the art can make various modifications and variations to the invention without departing from the spirit and scope of the invention. Thus the invention is also intended to encompass these modifications and variations therein as long as these modifications and variations come into the scope of the claims of the invention and their equivalents.

What is claimed is:

1. A reduction and fixation device for fracture correction, comprising: an aiming frame body comprising a fixation plate, a first rectangular frame, a support plate and a second rectangular frame, wherein a main guide tube is arranged in the fixation plate, a main nail is arranged in the main guide tube, a front end of the fixation plate is fixedly connected to one end of the first rectangular frame, two first sliding frames are slidingly arranged in the first rectangular frame, a first screw sleeve is arranged in the first sliding frame, upper and lower sides of the first screw sleeve are rotationally connected to an inner wall of the first sliding frame through a first rotating shaft, a first guide tube is arranged in the first screw sleeve, a first screw is arranged in the first guide tube, the support plate is vertically arranged on an upper end of the fixation plate, the second rectangular frame is fixedly arranged on an upper end of the support plate, a second sliding frame is slidingly arranged in the second rectangular frame, a second screw sleeve is arranged in the second sliding frame, front and rear sides of the second screw sleeve are rotationally connected to an inner wall of the second sliding frame through a second rotating shaft, a second guide tube is arranged in the second screw sleeve, and a second screw is arranged in the second guide tube;

an inner wall of the first screw sleeve is provided with a first internal thread, an outer wall of the first guide tube is provided with a first external thread, the first guide tube is connected to the first screw sleeve by threaded transmission, an inner wall of the second screw sleeve is provided with a second internal thread, an outer wall of the second guide tube is provided with a second external thread, and the second guide tube is connected to the second screw sleeve by threaded transmission;

a rear end of the first guide tube is sheathed with a rotating ring, the rotating ring is connected to the outer wall of the first guide tube by threaded transmission, a rear end of the rotating ring is fixedly provided with a fixation tube the fixation tube is sheathed outside the first guide tube, an inner diameter of the fixation tube is larger than an outer diameter of the first guide tube, a rear side wall of the fixation tube is provided with several first balls, the several first balls are distributed in a circular array with respect to a center of a rear side of the fixation tube, several pressing components are arranged behind the fixation tube, the several pressing components are distributed in a circular array with respect to a center of the first guide tube, the pressing components comprise a hinged plate, a pressing plate and a first spring, one end of the hinged plate is hingedly connected to the outer wall of the first guide tube, the pressing plate is located behind the hinged plate, the first spring is located between the pressing plate and the hinged plate, several first springs are provided, one end of the first spring is fixedly connected to a front side wall of the pressing plate, and other end of the first spring is fixedly connected to a rear side wall of the hinged plate.

2. The reduction and fixation device for fracture correction according to claim 1, wherein the first rotating shaft is symmetrically arranged on the upper and lower sides of the first screw sleeve, and one end of the first rotating shaft is fixedly connected to an outer wall of the first screw sleeve, and other end of the first rotating shaft is rotationally connected to the inner wall of the first sliding frame; the second rotating shaft is symmetrically arranged on the front and rear sides of the second screw sleeve), one end of the second rotating shaft is fixedly connected to an outer wall of the second screw sleeve, and other end of the second rotating shaft is rotationally connected to the inner wall of the second sliding frame.

3. The reduction and fixation device for fracture correction according to claim 1, wherein two first threaded holes and one second threaded hole are arranged through the main nail, the first threaded holes are adapted to the first screw, and the second threaded hole is adapted to the second screw.

4. The reduction and fixation device for fracture correction according to claim 2, wherein the two first sliding frames slide left and right along an inner wall of the first rectangular frame, a first screw rod is rotationally arranged on ends of the two first sliding frames away from each other, one end of the first screw rod away from the first sliding frame passes through an outer wall of the first rectangular frame, extends to outside of the first rectangular frame and is provided with a first knob, the first screw rod is connected to a penetration position of the first rectangular frame by threaded transmission; a second screw rod is rotationally arranged on a right side of the second sliding frame, one end of the second screw rod away from the second sliding frame passes through the second rectangular frame, extends to outside of the second rectangular frame and is provided with a second knob, and the second screw rod is connected to a penetration position of the second rectangular frame by threaded transmission.

5. The reduction and fixation device for fracture correction according to claim 1, wherein a horizontal plate is fixedly arranged on a rear end of the fixation plate and is perpendicular to the fixation plate, a third threaded hole and a guide hole are arranged in the horizontal plate, a third screw rod is arranged in the third threaded hole and is connected to the third threaded hole by threaded transmission, a front end of the third screw rod extends to the front of the horizontal plate and is rotationally provided with a clamping plate, a rear end of the third screw rod extends to the rear of the horizontal plate and is provided with a third knob, a guide rod is slidably arranged in the guide hole, one end of the guide rod is fixedly connected to a rear side wall of the clamping plate, a number of protection components are arranged at equal intervals in front of the clamping plate, the protection components comprise a cannula, a rear end of the cannula is fixedly connected to a front side wall of the horizontal plate, a sliding column is slidably arranged in the cannula, a guard plate is arrange on one end of the sliding column away from the cannula, a protective layer is fixedly arranged on a front side wall of the guard plate and is made of soft material, a second spring is arranged in the cannula, one end of the second spring is fixedly connected to a rear end of the sliding column (33), and other end of the second spring (36) is fixedly connected to an inner wall of the cannula (32).

6. The reduction and fixation device for fracture correction according to claim 5, wherein a limit assembly is arranged behind the horizontal plate and comprises a ratchet, the ratchet is fixedly arranged on the third screw rod, a fixation ring is arranged outside the ratchet, and an inner diameter of the fixation ring is larger than an outer diameter of the ratchet a connecting rod is arranged between the fixation ring and the guide rod (31), one end of the connecting rod is fixedly connected to the guide rod, and other end of the connecting rod is fixedly connected to an outer wall of the fixation ring; the fixation ring is provided with a through hole, a limit rod is slidably arranged in the through hole, one end of the limit rod extends to inside of the fixation ring and abuts against an outer wall of the ratchet, one end of the limit rod close to the ratchet is adapted to gear teeth of the ratchet, one end of the limit rod away from the ratchet extends to outside of the fixation ring and is provided with a limit plate, a third spring is sheathed on the limit rod, one end of the third spring is fixedly connected to the limit plate, and other end of the third spring is fixedly connected to the outer wall of the fixation ring.

7. The reduction and fixation device for fracture correction according to claim 4, further comprising a fixation assembly configured to limit rotation of the first rotating shaft, wherein the fixation assembly comprises two mounting plates arranged on one side of the first rotating shaft away from the first screw rod, the two mounting plates are vertically symmetrical about a center of the first screw sleeve, the mounting plate (43) is fixedly connected to the inner wall of the first sliding frame, a third rotating shaft is rotationally arranged on a front end of the mounting plate, a gear is fixedly arranged on a front end of the third rotating shaft, a first gear rack is arranged on one side of the gear close to the inner wall of the first sliding frame and meshes with the gear, a rear side wall of the first gear rack is slidingly connected to a front side wall of the mounting plate, one end of the first gear rack extends to one side of the first rotating shaft close to the first screw rod and is provided with a first splint, other end of the first gear rack is fixedly connected to one end of a fourth spring, other end of the fourth spring is fixedly connected to a fixed block fixedly arranged on the front side wall of the mounting plate, a second gear rack is arranged on one side of the gear away from the first gear rack and meshes with the gear, a rear side wall of the second gear rack is slidingly connected to the front side wall of the mounting plate, the second gear rack is close to one side of the first rotating shaft and is provided with a second splint, other end of the second gear rack is provided with a second ball, a contact plate is arranged on one side of the second ball away from the first rotating shaft, upper and lower ends of the contact plate abut against upper and lower second balls respectively, a fourth screw rod is arranged on one end of the contact plate away from the first rotating shaft, one end of the fourth screw rod away from the first rotating shaft passes through the first sliding frame, extends to outside of the first sliding frame and is provided with a fourth knob, and the fourth screw rod is connected to a penetration position of the first sliding frame by threaded transmission.

8. The reduction and fixation device for fracture correction according to claim 7, wherein the first gear rack and the second gear rack are symmetrically distributed about a center of the third rotating shaft, a first arc-shaped groove is arranged on one side of the first splint close to the first rotating shaft, a first arc-shaped plate is arranged in the first arc-shaped groove, a second arc-shaped groove is arranged on one side of the second splint close to the first rotating shaft, a second arc-shaped plate is arranged in the second arc-shaped groove, and the first arc-shaped plate and the second arc-shaped plate are both made of rubber non-slip material.

* * * * *